(12) United States Patent
Boutriau et al.

(10) Patent No.: US 9,233,151 B2
(45) Date of Patent: *Jan. 12, 2016

(54) VACCINE COMPOSITION (75) Inventors: Dominique Boutriau, Rixensart (BE); Carine Capiau, Rixensart (BE); Pierre Michel Desmons, Rixensart (BE); Dominique Lemoine, Rixensart (BE); Jan Poolman, Haarlem (NL)

(73) Assignee: GlaxoSmithKline Biologicals S.A., Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 13/439,829

(22) Filed: Apr. 4, 2012

(65) Prior Publication Data

US 2012/0207780 A1 Aug. 16, 2012

Related U.S. Application Data (62) Division of application No. 10/312,090, filed as application No. PCT/EP01/07288 on Jun. 27, 2001, now abandoned.

(30) Foreign Application Priority Data

| Jun. 29, 2000 | (GB) | .................................... | 0015999.6 |
| Apr. 3, 2001 | (GB) | .................................... | 0108363.3 |
| Apr. 3, 2001 | (GB) | .................................... | 0108364.1 |

(51) Int. Cl.
| *A61K 39/095* | (2006.01) |
| *A61K 39/116* | (2006.01) |
| *A61K 39/02* | (2006.01) |
| *A61K 47/48* | (2006.01) |
| *A61K 39/29* | (2006.01) |
| *A61K 39/102* | (2006.01) |
| *A61K 39/08* | (2006.01) |
| *A61K 39/05* | (2006.01) |
| *C07H 3/00* | (2006.01) |
| *A61K 39/385* | (2006.01) |
| *A61K 39/00* | (2006.01) |

(52) U.S. Cl.
CPC ......... *A61K 39/102* (2013.01); *A61K 2039/545* (2013.01); *A61K 2039/6037* (2013.01)

(58) Field of Classification Search
None
See application file for complete search history.

(56) References Cited

U.S. PATENT DOCUMENTS 8,398,983 B2 * 3/2013 Biemans et al. ........... 424/184.1

FOREIGN PATENT DOCUMENTS

| EP | 2279748 | 2/2011 |
| WO | 93/24148 | 12/1993 |
| WO | 97/00697 | 1/1997 |
| WO | 99/13906 | 3/1999 |
| WO | WO 99/48525 | * 9/1999 |

OTHER PUBLICATIONS

Langue et al., Eur. J. Pediatr. 158: 717-722, 1999.*
Paradiso et al., Pediatrics 92: 827-832, 1993.*
Granoff, et al., MF59 Adjuvant Enhances Antibody Responses of Infant Baboons Immunized with Haemophilus influenzae Type b and Neisseria meningitidis Group C Oligosaccharide-CRM197 Conjugate Vaccine, Infect & Immun 65(5):1710-1715 (1997).
Zepp, et al., Evidence for induction of polysaccharide specific B-cell-memory in the 1st year of life: plain Haemophilus influenzae type b—PRP (Hib) boosters children primed with a tetanus-conjugate Hib-DTPa-HBV combined vaccine, Eur J Pediatr 156:18-24 (1997).
Bravo, et al, The New DTPw-HBV-Hib Combination Vaccine Can Be Used at the Who Schedule with a Monovalent Dose of Hepatitis B Vaccine at Birth, Southeast Asian J Trop Med & Public Health 29(4):772-778 (1998).
Andre, Development and clinical application of new polyvalent combined paediatric vaccines, Vaccine 17 (13-14):1620-1627 (1999).
Pines, et al., New acellular pertussis-containing paediatric combined vaccines, Vaccine, 17(13-14):1650-1656 (1999).
Choo, et al., Immunogenicity and reactogenicity of a group C meningococcal conjugate vaccine compared with a group A + C meningococcal polysaccharide vaccine in adolescents in a randomized observer-blind controlled trial, Vaccine 18(24):2686-2692 (2000).
Fernandez, et al., Randomized Trial of the Immunogenicity of Fractional Dose Regimens of PRP-T Haemophilus Influenzae Type B Conjugate Vaccine, Am J Trop Med Hygiene, 62(4):485-490 (2000).
Maclennan, et al., Safety, Immunogenicity, and Induction of Immunologic Memory by a Serogroup C Meningococcal Conjugate Vaccine in Infants in a Randomized Controlled Trial, JAMA 283(21):2795-2801 (2000).

(Continued)

*Primary Examiner* — S. Devi
(74) *Attorney, Agent, or Firm* — Barbara J. Carter (57) ABSTRACT

A multi-valent vaccine composition is described comprising a conjugate of the capsular polysaccharide of *H. influenzae* b not adsorbed onto an aluminum adjuvant salt, and two or more further bacterial polysaccharides. A multi-valent vaccine composition is also described comprising a whole-cell pertussis component, tetanus toxoid, diphtheria toxoid, Hepatitis B surface antigen, a conjugate of the capsular polysaccharide of *H. influenzae* b, and a conjugate of a capsular polysaccharide of *N. meningitidis* type A or C (or both). Furthermore, a multi-valent vaccine composition is described comprising a whole-cell pertussis component, tetanus toxoid, diphtheria toxoid, and a low dose of a conjugate of the capsular polysaccharide of *H. influenzae* b.

10 Claims, 5 Drawing Sheets

(56) References Cited

OTHER PUBLICATIONS

Richmond, et al., Safety and immunogenicity of a new Neisseria meningitidis serogroup C-tetanus toxoid conjugate vaccine in healthy adults, Vaccine 18:641-646 (2000).

Corresponding E.P. Application No. 10178449.4 filed Sep. 22, 2010, published Feb. 2, 2011 as Publication No. EP227948, cited above.
European Search Report and Opinion dated 10 Dec. 2010 for EP Application No. 10178449.4, Publication No. EP227948 (Corresponding EP equivalent of present case).

* cited by examiner

Figure 3

VACCINE COMPOSITION

This application is filed pursuant to 35 U.S.C. §111(a) as a U.S. Divisional Application of U.S. application Ser. No. 10/312,090 filed Mar. 26, 2003, now abandoned, which is a §371 U.S. National Phase Application of International Patent Application Serial No. PCT/EP2001/07288 filed Jun. 27, 2001, which claims priority to Great Britain Application No. 0015999.6 filed Jun. 29, 2000, Great Britain Application No. 0108363.3 filed Apr. 3, 2001, and Great Britain Application No. 0108364.1 filed Apr. 3, 2001, the contents of which are all incorporated herein by reference.

BACKGROUND

The present invention relates to new combination vaccine formulations. Combination vaccines (which provide protection against multiple pathogens) are very desirable in order to minimise the number of immunisations required to confer protection against multiple pathogens, to lower administration costs, and to increase acceptance and coverage rates. The well-documented phenomenon of antigenic competition (or interference) complicates the development of multi-component vaccines. Antigenic interference refers to the observation that administering multiple antigens often results in a diminished response to certain antigens relative to the immune response observed when such antigens are administered individually.

Combination vaccines are known which can prevent *Bordetella pertussis, Clostridium tetani, Corynebacterium diphtheriae*, and optionally Hepatitis B virus and/or *Haemophilus influenzae* type b (see, for instance, WO 93/24148 and WO 97/00697).

SUMMARY

The present invention concerns the manufacture of the most ambitious multi-valent vaccines to date, the administration of which can prevent or treat infection by *Bordetella pertussis, Clostridium tetani, Corynebacterium diphtheriae*, Hepatitis B virus, *Haemophilus influenzae* and *N. meningitidis*, and preferably also Hepatitis A virus and/or Polio virus, wherein the components of the vaccine do not significantly interfere with the immunological performance of any one component of the vaccine.

DETAILED DESCRIPTION

Accordingly, in one aspect the present invention provides a multi-valent immunogenic composition for conferring protection in a host against disease caused by *Bordetella pertussis, Clostridium tetani, Corynebacterium diphtheriae*, Hepatitis B virus, *Haemophilus influenzae* and *N. meningitidis* comprising:
  (a) either killed whole-cell *Bordetella pertussis* (Pw), or two or more acellular pertussis components (Pa) [preferably the former],
  (b) tetanus toxoid (TT),
  (c) diphtheria toxoid (DT),
  (d) Hepatitis B surface antigen (HepB),
  (e) a conjugate of a carrier protein and the capsular polysaccharide of *H. influenzae* type B (Hib), and
  (f) one or more conjugates of a carrier protein and a capsular polysaccharide of a bacterium selected from the group *N. meningitidis* type A (MenA) and *N. meningitidis* type C (MenC).

Methods of preparing tetanus toxoid (TT) are well known in the art. For instance, TT is preferably produced by purification of the toxin from a culture of *Clostridium tetani* followed by chemical detoxification, but is alternatively made by purification of a recombinant, or genetically detoxified analogue of the toxin (for example, as described in EP 209281). 'Tetanus toxoid' also encompasses immunogenic fragments of the full-length protein (for instance Fragment C—see EP 478602).

Methods of preparing diphtheria toxoid (DT) are also well known in the art. For instance, DT is preferably produced by purification of the toxin from a culture of *Corynebacterium diphtheriae* followed by chemical detoxification, but is alternatively made by purification of a recombinant, or genetically detoxified analogue of the toxin (for example, CRM197, or other mutants as described in U.S. Pat. No. 4,709,017, U.S. Pat. No. 5,843,711, U.S. Pat. No. 5,601,827, and U.S. Pat. No. 5,917,017).

Acellular pertussis components (Pa) are well known in the art. Examples include pertussis toxoid (PT), filamentous haemagluttinin (FHA), pertactin (PRN) and agglutinogens 2 and 3. These antigens are partially or highly purified. Preferably 2 or more acellular pertussis components are used in the vaccine. More preferably 2, 3, 4 or all 5 of the above example acellular pertussis components are incorporated in the vaccine. Most preferably PT, FHA and PRN are included. PT may be produced by a variety of manners, for instance by purification of the toxin from a culture of *B. pertussis* followed by chemical detoxification, or alternatively by purification of a genetically detoxified analogue of PT (for example, as described in U.S. Pat. No. 5,085,862).

Methods of preparing killed, whole-cell *Bordetella pertussis* (Pw) suitable for this invention is disclosed in WO 93/24148, as are suitable formulation methods for producing DT-TT-Pw-HepB and DT-TT-Pa-HepB vaccines.

The bacterial capsular polysaccharide conjugates may comprise any carrier peptide, polypeptide or protein comprising at least one T-helper epitope. Preferably the carrier protein(s) used is selected from the group comprising: tetanus toxoid, diphtheria toxoid, CRM197, recombinant diphtheria toxin (as described in any of U.S. Pat. No. 4,709,017, WO 93/25210, WO 95/33481, or WO 00/48638), pneumolysin (preferably chemically detoxified, or a detoxified mutant) from *S. pneumoniae*, OMPC from *N. meningitidis*, and protein D (PD) from *H. influenzae* (EP 594610). Due to the known effect of carrier suppression, it is advantageous if in each of the compositions of the invention the polysaccharide antigens contained therein ('n' antigens) are conjugated to more than one carrier. Thus (n-1) of the polysaccharides could be carried (separately) on one type of carrier, and 1 on a different carrier, or (n-2) on one, and 2 on two different carriers, etc. For example, in a vaccine containing 4 bacterial polysaccharide conjugates, 1, 2 or all four could be conjugated to different carriers). Protein D, however, is advantageously used as a carrier in the compositions of the invention as it may be used for various (2, 3, 4 or more) polysaccharides in a composition without a marked carrier suppression effect. Most preferably Hib is present as a TT conjugate, and MenA, MenC, MenY and MenW are either TT or PD conjugates. Protein D is also a useful carrier as it provides a further antigen which can provide protection against *H. influenzae*.

The polysaccharide may be linked to the carrier protein by any known method (for example, by Likhite, U.S. Pat. No. 4,372,945 and by Armor et al., U.S. Pat. No. 4,474,757). Preferably, CDAP conjugation is carried out (WO 95/08348).

In CDAP, the cyanylating reagent 1-cyano-dimethylaminopyridinium tetrafluoroborate (CDAP) is preferably used for the synthesis of polysaccharide-protein conjugates. The cyanilation reaction can be performed under relatively mild conditions, which avoids hydrolysis of the alkaline sensitive polysaccharides. This synthesis allows direct coupling to a carrier protein.

The above immunogenic composition may further comprise one, two, three, four, five, six or seven components selected from the following list: *N. meningitidis* type Y polysaccharide [MenY] (preferably conjugated), *N. meningitidis* type W polysaccharide [MenW] (preferably conjugated), the Vi polysaccharide of *Salmonella typhi*, *N. meningitidis* (preferably serotype B) outer membrane vesicles, one or more *N. meningitidis* (preferably serotype B) outer membrane (surface-exposed) proteins, killed, attenuated Hepatitis A virus (HepA—preferably the product known as HAVRIX® [SmithKline Beecham Biologicals]), and inactivated polio virus (IPV—preferably comprising types 1, 2 and 3 as is standard in the vaccine art, most preferably the Salk polio vaccine) without substantial interference problems for any of the antigens of the composition.

The immunogenic compositions of the invention are preferably formulated as a vaccine for in vivo administration to the host in such a way that the individual components of the composition are formulated such that the immunogenicity of individual components is not substantially impaired by other individual components of the composition. By not substantially impaired, it is meant that upon immunisation, an antibody titre against each component is obtained which is more than 60%, preferably more than 70%, more preferably more than 80%, still more preferably more than 90%, and most preferably more than 95-100% of the titre obtained when the antigen is administered in isolation.

The immunogenic compositions of the invention are preferably formulated as a vaccine for in vivo administration to the host, such that they confer an antibody titre superior to the criterion for seroprotection for each antigenic component for an acceptable percentage of human subjects. This is an important test in the assessment of a vaccine's efficacy throughout the population. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

The immunogenic composition of the invention are preferably adjuvanted. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes.

The adjuvant may also be selected to be a preferential inducer of a TH1 type of response to aid the cell mediated branch of the immune response.

High levels of Th1-type cytokines tend to favour the induction of cell mediated immune responses to a given antigen, whilst high levels of Th2-type cytokines tend to favour the induction of humoral immune responses to the antigen.

Suitable adjuvant systems which promote a predominantly Th1 response include, Monophosphoryl lipid A or a derivative thereof, particularly 3-de-O-acylated monophosphoryl lipid A, and a combination of monophosphoryl lipid A, preferably 3-de-O-acylated monophosphoryl lipid A (3D-MPL) together with an aluminium salt. An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210. The vaccine may additionally comprise a saponin, more preferably QS21. The formulation may also comprises an oil in water emulsion and tocopherol (WO 95/17210). Unmethylated CpG containing oligonucleotides (WO 96/02555) are also preferential inducers of a TH1 response and are suitable for use in the present invention.

Aluminium salts are preferred adjuvants in the above immunogenic compositions. In particular, HepB should preferably be adsorbed onto aluminium phosphate before admixing with the other components. In order to minimise the levels of adjuvant (particularly aluminium salts) in the compositions of the invention, the polysaccharide conjugates may be unadjuvanted.

The present invention also provides a method for producing a vaccine formulation comprising the step of mixing the components of the vaccine together with a pharmaceutically acceptable excipient.

A particularly preferred DTPw composition of the invention comprises: TT, DT, Pw, HepB (preferably adsorbed onto aluminium phosphate), Hib (preferably conjugated onto TT and/or unadsorbed), MenA (preferably conjugated onto protein D), and MenC (preferably conjugated onto protein D). Preferably the vaccine may be supplied in 2 containers, the first containing DTPw-HepB in a liquid form, and a second containing Hib-MenA-MenC in a lyophilised form. The contents of the containers may be mixed extemporaneously before administering to a host in a single injection.

In a further aspect of the present invention there is provided an immunogenic composition or vaccine as herein described for use in a medicament.

In a still further aspect of the invention there is provided a use of the immunogenic compositions of the invention in the manufacture of a medicament for the treatment or prevention of diseases caused by infection by *Bordetella pertussis*,

*Clostridium tetani, Corynebacterium diphtheriae*, Hepatitis B virus, *Haemophilus influenzae* and *N. meningitidis*.

Additionally, a method of immunising a human host against disease caused by *Bordetella pertussis, Clostridium tetani, Corynebacterium diphtheriae*, Hepatitis B virus, *Haemophilus influenzae* and *N. meningitidis*, which method comprises administering to the host an immunoprotective dose of the immunogenic composition of the invention is also provided.

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts.

The amount of antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 0.1-100 µg of polysaccharide, preferably 0.1-50 µg, preferably 0.1-10 µg, of which 1 to 5 µg is the most preferable range.

The content of protein antigens in the vaccine will typically be in the range 1-100 µg, preferably 5-50 µg, most typically in the range 5-25 µg.

Following an initial vaccination, subjects may receive one or several booster immunisations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

Interestingly, the inventors have also found that for vaccines comprising TT, DT, Pw and Hib, surprisingly a substantially lower dose of Hib can be used in the combination vaccine (compared with the standard dose of 10 µg per 0.5 mL dose) to obtain at least equivalent antibody titres against the *H. influenzae* type b capsular polysaccharide antigen. This is contrary to what would have been expected.

Accordingly, in a further embodiment of the invention there is provided a multi-valent immunogenic composition comprising killed whole-cell *Bordetella pertussis* (Pw), tetanus toxoid (TT), diphtheria toxoid (DT), and a conjugate of a carrier protein and the capsular polysaccharide of *H. influenzae* type B (Hib—preferably conjugated to TT, DT or CRM197), wherein the amount of conjugate per 0.5 mL dose of bulk vaccine is 1-8 µg, and the immunogenicity of the conjugate is equivalent or improved over such compositions comprising larger amounts of conjugate. Optionally, Hepatitis B surface antigen may also be included.

Preferably the amount of conjugate per 0.5 mL dose of bulk vaccine is less than 10 µg (of polysaccharide in the conjugate), more preferably 1-7 or 2-6 µg, and most preferably about 2.5, 3, 4 or 5 µg. Most preferably the Hib conjugate is not adsorbed onto aluminium adjuvant salt before being mixed with the DTPw vaccine.

A further observation that the inventors have made is the fact that combination vaccines comprising a Hib conjugate elicits significantly higher anti-Hib antibody titres in a host (compared with a monovalent, unadsorbed Hib conjugate vaccine) if the Hib conjugate is administered in a vaccine additionally comprising 1, but particularly 2 or more additional bacterial polysaccharides and the Hib polysaccharide (and preferably all the polysaccharides) of the vaccine are not adsorbed onto an adjuvant (particularly aluminium salts).

A further, independent, aspect of the invention therefore is the provision of a multi-valent immunogenic composition comprising a conjugate of a carrier protein and the capsular polysaccharide of *H. influenzae* type B (Hib), wherein said composition additionally comprises 1, but particularly 2 or more further bacterial polysaccharides (preferably more than 2, 3, 4, 5, 6, 7, 8, 9, 10, 11, 12, or 13) capable of conferring protection to a host against infection by the bacteria from which they are derived, and wherein the Hib polysaccharide (and preferably none of said polysaccharides) in the composition are adsorbed onto an aluminium adjuvant salt. Most preferably there is no aluminium adjuvant salt present in the composition.

By an antigen not being 'adsorbed onto an aluminium adjuvant salt' it is meant that an express or dedicated adsorption step for the antigen on fresh aluminium adjuvant salt is not involved in the process of formulating the composition.

Hib may be conjugated to any carrier which can provide at least one T-helper epitope (examples of which are described above), and preferably tetanus toxoid.

Preferably, the further bacterial polysaccharides are also conjugated to a carrier protein (examples of which are described above). In specific embodiments the capsular polysaccharide of *H. influenzae* type B and the further polysaccharides are not conjugated to the same carrier (Hib and none of the further polysaccharides share the same carrier), particularly where the carrier is CRM197. In the preferred embodiments of the examples at least one of the polysaccharides of the composition is conjugated onto protein D, however this is not essential for the performance of the invention—indeed neither the Hib nor any of the further polysaccharides need be conjugated onto protein D.

In a specific embodiment of the above invention, only Hib and further bacterial polysaccharides (and conjugates thereof) are the only antigens present in the composition.

An amount of polysaccharide which capable of conferring protection to a host (an effective amount) can be readily determined by the skilled person. Generally, it is expected that each dose will comprise 0.1-100 µg of polysaccharide, preferably 0.1-50 µg, preferably 0.1-10 of which 1 to 5 µg is the most preferable range. The Hib conjugate is preferably present in an amount of 3-15 µg (of polysaccharide in the conjugate), more preferably 4-12 µg and most preferably 5-10 µg. In a preferred embodiment a total of no less than 2 µg of further polysaccharide (particularly when conjugated) is present in the composition per 0.5 mL dose, and preferably no less than 3, 4, 5, 6, 7, 8, 9, 10, 11, 12, 13, 14, 15, 17, 20, 25, 30, 35, 40, 45 or 50 µg are included. Preferably no more than 100 µg of further polysaccharide are included per 0.5 mL dose.

Preferably the further bacterial polysaccharides are selected from a group consisting of: *N. meningitidis* serogroup A capsular polysaccharide (MenA), N meningitidis serogroup C capsular polysaccharide (MenC), *N. meningitidis* serogroup Y capsular polysaccharide (MenY), *N. meningitidis* serogroup W capsular polysaccharide (MenW), Group B *Streptococcus* group I capsular polysaccharide, Group B *Streptococcus* group II capsular polysaccharide, Group B *Streptococcus* group III capsular polysaccharide, Group B *Streptococcus* group IV capsular polysaccharide, Group B *Streptococcus* group V capsular polysaccharide, *Staphylococcus aureus* type 5 capsular polysaccharide, *Staphylococcus aureus* type 8 capsular polysaccharide, Vi polysaccharide from *Salmonella typhi, N. meningitidis* LPS, *M. catarrhalis* LPS, and *H. influenzae* LPS. By LPS it is meant either native lipo-polysaccharide (or lipo-oligosaccharide), or lipo-polysaccharide where the lipid A portion has been detoxified by any of a number of known methods (see for example WO 97/18837 or WO 98/33923), or any molecule comprising the O-polysaccharide derived from said LPS. By *N. meningitidis* LPS it is meant one or more of the 12 known immunotypes (L1, L2, L3, L4, L5, L6, L7, L8, L9, L10, L11 or L12).

Particularly preferred combinations are compositions containing or comprising: 1) conjugated Hib, conjugated MenA and conjugated MenC; 2) conjugated Hib, conjugated MenY and conjugated MenC; and 3) conjugated Hib and conjugated MenC. The amount of PS in each of the above conjugates may be 5 or 10 μg each per 0.5 mL human dose. Optionally, the above compositions may also include *N. meningitidis* serotype B outer membrane vesicles, or one or more *N. meningitidis* serotype B outer membrane (surface-exposed) proteins, or one or more *N. meningitidis* LPS (as defined above) to make a global meningitis vaccine. Preferably MenA, MenC and MenY are either TT or PD conjugates.

The further bacterial polysaccharides may also be selected from any of the capsular pneumococcal polysaccharides (preferably more than 7, more preferably 11 or more, and most preferably 13 or more) such as from serotype: 1, 2, 3, 4, 5, 6A, 6B, 7F, 8, 9N, 9V, 10A, 11A, 12F, 14, 15B, 17F, 18C, 19A, 19F, 20, 22F, 23F or 33F. Preferably the pneumococcal polysaccharides are conjugated (most preferably PD conjugates).

For instance pneumococcal polysaccharides derived from at least four serotypes (including 6B, 14, 19F and 23F for example), or from at least 7 serotypes (including 4, 6B, 9V, 14, 18C, 19F, and 23F for example) may be selected from the above list. More preferably polysaccharides from more than 7 serotypes are included in the composition, for instance at least 11 serotypes. For example the composition in one embodiment includes 11 capsular polysaccharides derived from serotypes 1, 3, 4, 5, 6B, 7F, 9V, 14, 18C, 19F and 23F (preferably conjugated). In a preferred embodiment of the invention at least 13 polysaccharide antigens (preferably conjugated) are included, although further polysaccharide antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

For elderly vaccination (for instance for the prevention of pneumonia) it is advantageous to include serotypes 8 and 12F (and most preferably 15 and 22 as well) to the preferred 11 valent antigenic composition described above to form a 13/15 valent vaccine, whereas for infants or toddlers (where otitis media is of more concern) serotypes 6A and 19A are advantageously included to form a 13 valent vaccine.

The pneumococcal polysaccharides may or may not be adsorbed onto aluminium adjuvant salts.

Hib (preferably lyophilised) and the pneumococcal polysaccharides (preferably in a liquid form) may be mixed extemporaneously before administering to a host in a single administration/injection. With such a formulation it is possible, upon immunisation, to obtain antibody titres against Hib capsular polysaccharide in excess of 100% of the titre obtained when the Hib conjugate is administered in isolation. In preferred embodiments, no (significantly) detrimental effect occurs to the pneumococcal polysaccharide conjugates (in terms of protective efficacy) in the combination as compared to their administration in isolation. This can be assessed in terms of measuring post-primary geometric mean concentrations (GMC) of anti-polysaccharide antibody 1 month after the last primary dose (primary doses being the priming administrations—usually 3—in the first year of life). The GMC (in μg/ml) for a vaccine of the invention should be preferably over 55% (more preferably over 60, 70, 80, or 90%) of the GMC when the pneumococcal polysaccharides are administered without the Hib conjugate. Another indication that no detrimental effect has occurred is if the % of subjects with antibody concentrations of no less than 0.5 μg/ml differs by no more than 10% (preferably less than 9, 7, 5, 3 or 1%) when comparing 1 month post-primary administrations of the vaccine of the invention versus the vaccine without Hib conjugate.

Although the above refers to Hib and further bacterial 'polysaccharides' (the preferred embodiment) it is envisaged that the invention may be extended to Hib and further bacterial 'oligosaccharides' (which naturally have a low number of repeat units, or which are polysaccharides reduced in size for manageability, but are still capable of inducing a protective immune response in a host) which are well known in the vaccine art.

Preferably, the multi-valent immunogenic composition of this aspect of the invention is formulated as a vaccine for in vivo administration to the host wherein the individual components of the composition are formulated such that the immunogenicity of individual components is not impaired by other individual components of the composition (see above definition). Thus, in preferred embodiments, no (significantly) detrimental effect occurs to the further bacterial polysaccharides (in terms of protective efficacy) in the combination as compared to their administration in isolation.

Preferably, the multi-valent immunogenic composition of this aspect of the invention is formulated as a vaccine for in vivo administration to the host, which confers an antibody titre superior to the criterion for seroprotection for each antigenic component for an acceptable percentage of human subjects (see above definition).

The compositions of this aspect of the invention are preferably formulated in a vaccine. The use of the of the multi-valent immunogenic composition of this aspect of the invention in the manufacture of a medicament for the treatment or prevention of diseases caused by infection by *Haemophilus influenzae* (and preferably also those organisms from which the further bacterial polysaccharides are derived) is also envisioned, as is a method of immunising a human host against disease caused by *Haemophilus influenzae* (and preferably also those organisms from which the further bacterial polysaccharides are derived), which method comprises administering to the host an immunoprotective dose of the multi-valent immunogenic composition of this aspect of the invention.

A process for making the multi-valent immunogenic composition of this aspect of the invention is also provided, comprising the step of mixing together the individual components. If the further bacterial polysaccharides are to be adsorbed onto an aluminium adjuvant salt, this should be done before Hib is added to the formulation. Preferably an excess of aluminium adjuvant salt should not be used. Most preferably the Hib should be added to the aluminium adjuvanted further polysaccharide extemporanoeusly to the composition being administered to a host.

All cited references and publications are incorporated by reference herein.

EXAMPLES

Examples are provided solely for the purposes of illustration and are not intended to limit the scope of the invention.

Example 1

Preparation of a DT-TT-Pw-HepB (DTPw-HepB) Vaccine

This was done as described in WO 93/24148. The vaccine is commercially available under the name TRITANRIX-HEPB™ (SmithKline Beecham Biologicals).

Example 2

Preparation of MenA-MenC-Hib (MenAC-Hib) Vaccines i) Unadjuvanted MenC-Hib or MenA-MenC-Hib MenAC-Hib: *N. meningitidis* type A capsular polysaccharide conjugated onto protein D (using the CDAP technique), *N. meningitidis* type C capsular polysaccharide conjugated onto protein D and *H. influenzae* type b capsular polysaccharide conjugated onto TT were mixed together in an amount of 5 μg of each polysaccharide in each conjugate per 0.5 mL human dose. The pH was adjusted to 6.1, and was lyophilised in the presence of sucrose.

MenC-Hib: *N. meningitidis* type C capsular polysaccharide conjugated onto protein D (using the CDAP technique) and *H. influenzae* type b capsular polysaccharide conjugated onto TT were mixed together in an amount of 5 μg of polysaccharide in each conjugate per 0.5 mL human dose. The pH was adjusted to 6.1, and was lyophilised in the presence of sucrose.

ii) Adjuvanted MenA-MenC-Hib

*N. meningitidis* type A capsular polysaccharide conjugated onto protein D (using the CDAP techniques), *N. meningitidis* type C capsular polysaccharide conjugated onto protein D and *H. influenzae* type b capsular polysaccharide conjugated onto TT were each adsorbed separately in saline onto aluminium phosphate (5 μg of each conjugate onto 100 μg, 100 μg and 60 μg $Al^{3+}$, respectively, per dose). The adsorbed vaccines were mixed together at a pH of 6.1 and were lyophilised in the presence of sucrose.

Example 3

Clinical Trial

Study MenAC-Hib 001 evaluates the immunogenicity, reactogenicity and safety induced by MenC-Hib and MenAC-Hib (adsorbed and unadsorbed) made by the above example given as a three-dose primary vaccination in infants.

The study was a phase II, randomized study and included five study groups. The formulations that were evaluated were a lyophilized plain and adsorbed formulation of MenAC-Hib and a plain formulation of MenC-Hib. These three formulations were administered to the three first study groups of infants at 3, 4 and 5 months of age; TRITANRIX-HEPB™ was given concomitantly (as a separate injection) to these three groups. The plain formulation of MenAC-Hib was also reconstituted within a liquid diphtheria, tetanus, whole-cell pertussis, hepatitis B combined vaccine TRITANRIX-HEPB™) and administered as a single injection to the fourth study group of infants at 3, 4 and 5 months of age. The fifth group (control) was administered TRITANRIX-HEPB™-Hib vaccine at 3, 4, 5 months of age. The study was open, but the two first groups receiving the two different formulations of MenAC-Hib were double-blind, as well as the two last groups receiving the TRITANRIX-HEPB™-MenAC-Hib and the TRITANRIX-HEPB™-Hib vaccines. In summary the study groups were:

| Group A | $MenA_{5\mu g}C_{5\mu g}$-$Hib_{5\mu g}$ + DTPw-HepB | N = 80 |
|---|---|---|
| Group B | $MenA_{5\mu g}C_{5\mu g}$-$Hib_{5\mu g}$ adsorbed + DTPw-HepB | N = 80 |
| Group C | $MenC_{5\mu g}$-$Hib_{5\mu g}$ + DTPw-HepB | N = 80 |
| Group D | DTPw-HepB/$MenA_{5\mu g}C_{5\mu g}$-$Hib_{5\mu g}$ | N = 80 |
| Group E | DTPw-HepB/$MenA_{5\mu g}C_{5\mu g}$-HIBERIX ® | N = 80 |

The results showed that each formulation that was evaluated induced a good immune response against each antigen (antibodies against meningococcal groups A and C, Poly-Ribosyl-Phosphate (the capsular polysaccharide of *H. influenzae* type b), Diphtheria toxoid, Tetanus toxoid, Bordetella pertussis and hepatitis B were measured). Each vaccine formulation was well tolerated.

Post III Anti Poly-Ribosyl-Phosphate (PRP)

| Group | ≥0.15 mcg/ml % [L.L.-U.L.] | ≥1.0 mcg/ml % [L.L.-U.L.] | GMC (mcg/ml) [L.L.-U.L.] |
|---|---|---|---|
| MenAC-Hib | 98.5 | 98.5 | 19.0 |
| N = 67 | [92.0-100.0] | [92.0-100.0] | [13.7-26.3] |
| MenAC-Hib_ads | 100.0 | 90.1 | 7.6 |
| N = 71 | [94.9-100.0] | [80.7-95.9] | [5.6-10.7] |
| MenC-Hib | 100.0 | 95.5 | 12.6 |
| N = 66 | [94.6-100.0] | [87.3-99.1] | [9.2-17.2] |
| DTPw-HepB/MenAC-Hib | 98.5 | 94.0 | 8.7 |
| N = 67 | [92.0-100.0] | [85.4-98.3] | [6.2-12.2] |
| DTPw-HepB/HIBERIX ® | 98.6 | 92.8 | 7.5 |
| N = 69 | [92.2-100.0] | [83.9-97.6] | [5.5-11.3] |

Figure 1:
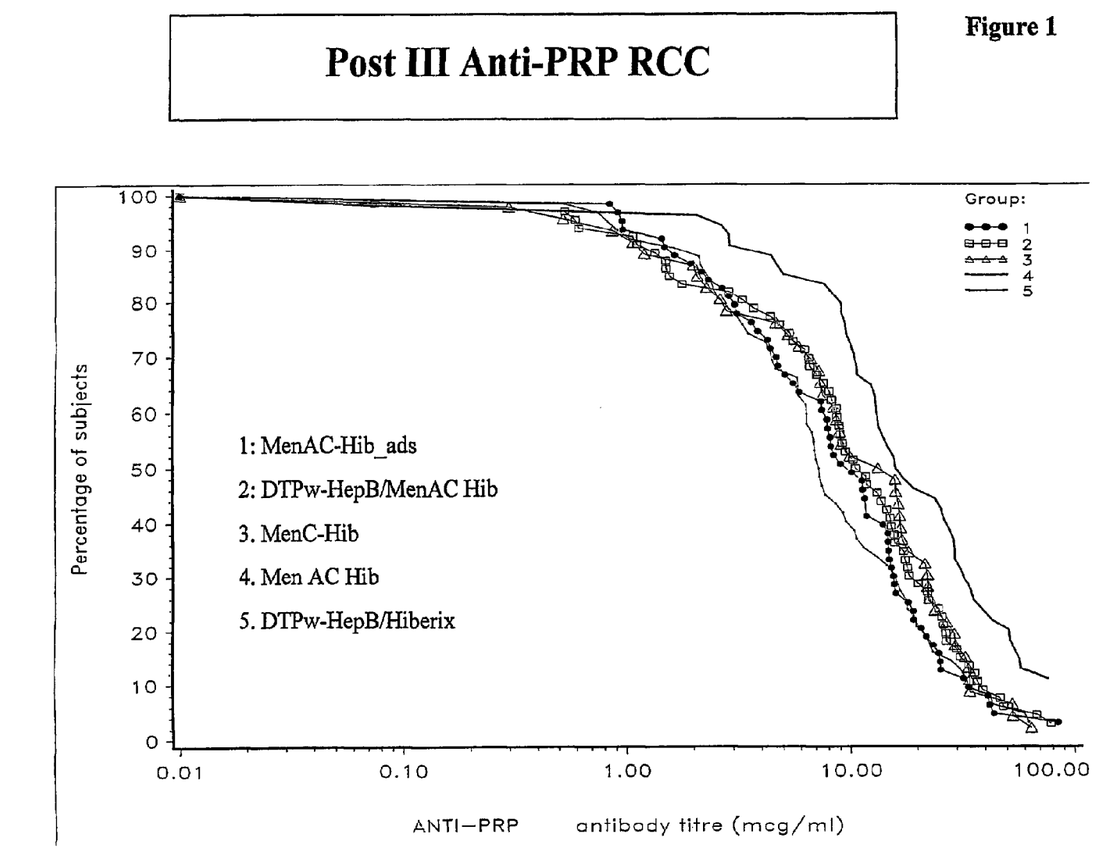
FIG. 1 is a graph (reverse cumulative curve) of the anti-PRP (poly-ribosyl-phosphate) antibody titre (mcg/ml) for each study group of Example 3, showing the percentage of subjects in each study group attaining the antibody titre levels.

0.15 and 1.0 mcg/ml are typical titre thresholds which are observed to estimate seroprotection. There is no Hib interference in the DTPw-HepB/MenAC-Hib vaccine. This can also be seen in FIG. 1 which shows the reverse cumulative curve (RCC) of the data. In addition, it is surprising that the non-adsorbed MenAC-Hib vaccine displayed significantly higher anti PRP titre compared with the adsorbed formulation.

Post III Anti Protein D IgG

| Group | ≥100 ELU/ml % [L.L.-U.L.] | GMC (ELU/ml) [L.L.-U.L.] |
|---|---|---|
| MenAC-Hib | 96.9 | 842 |
| N = 64 | [89.2-99.6] | [662-1072] |
| MenAC-Hib_ads | 100.0 | 1480 |
| N = 66 | [94.6-100.0] | [1195-1831] |
| MenC-Hib | 95.2 | 550 |
| N = 63 | [86.7-99.0] | [426-709] |
| DTPw-HepB/MenAC-Hib | 100 | 1815 |
| N = 63 | [94.3-100.0] | [1411-2335] |
| DTPw-HepB/HIBERIX ® | 14.1 | 62.1 |
| N = 64 | [6.6-25.0] | [54-72] |

Figure 2:
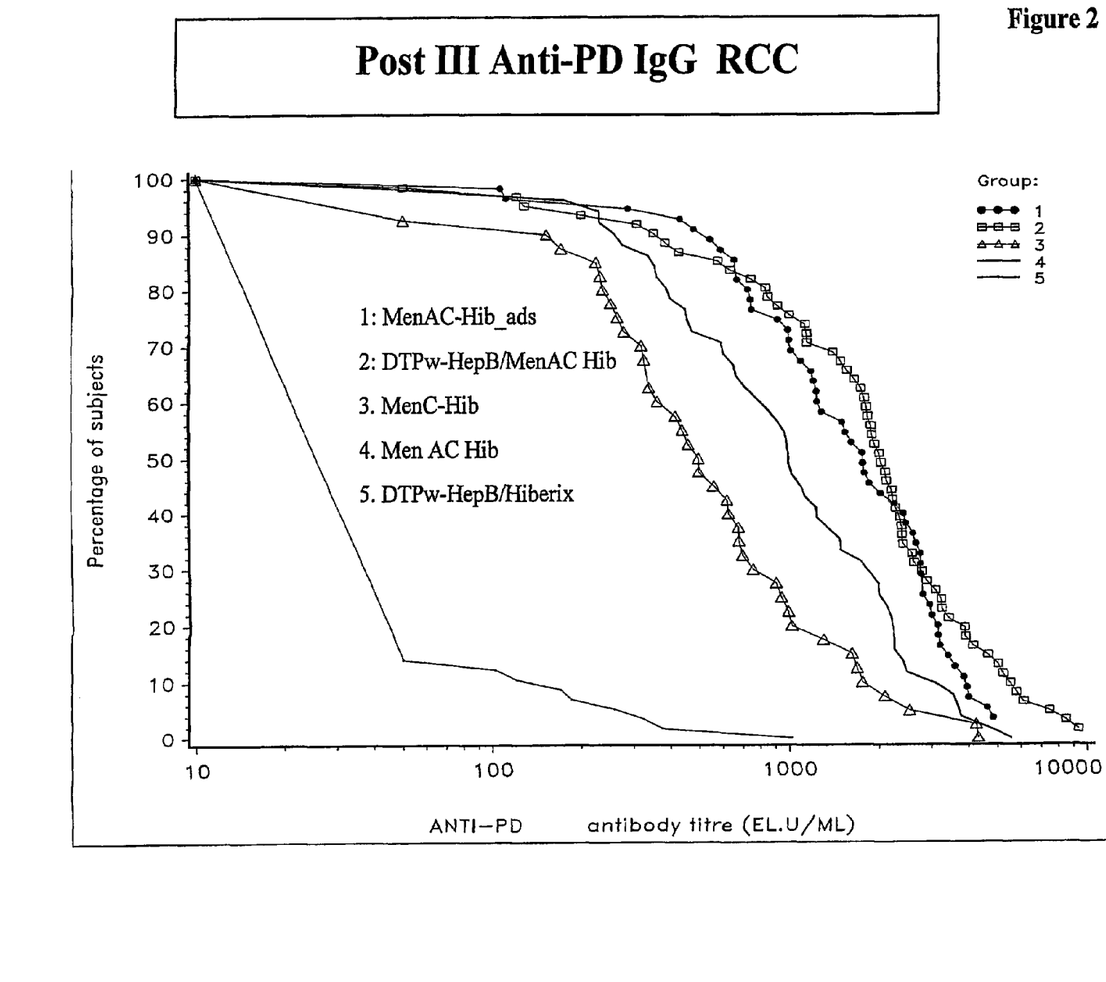
FIG. 2 is a graph (reverse cumulative curve) of the anti-PD (Protein D carrier protein) IgG antibody titre (ELU/ml) for each study group of Example 3, showing the percentage of subjects in each study group attaining the antibody titre levels.

See also FIG. 2 for the respective RCC anti-PD IgG curves. As can be seen, all formulations induced an immune response to the carrier protein (protein D).

Post III Anti PSA (Capsular Polysaccharide of Meningococcus A) IgG

| Group | ≥0.3 mcg/ml % [L.L.-U.L.] | GMC (mcg/ml) [L.L.-U.L.] |
|---|---|---|
| MenAC-Hib | 100.0 | 7.4 |
| N = 52 | [93.2-100.0] | [6.0-9.1] |
| MenAC-Hib_ads | 100.0 | 9.8 |
| N = 55 | [93.5-100.0] | [7.9-12.2] |
| MenC-Hib | 17.9 | 0.22 |
| N = 39 | [7.5-33.5] | [0.16-0.29] |
| DTPw-HepB/MenAC-Hib | 98.4 | 15.1 |
| N = 61 | [91.2-100.0] | [11.5-19.9] |
| DTPw-HepB/HIBERIX ® | 3.5 | 0.16 |
| N = 57 | [0.4-12.1] | [0.14-0.18] |

Figure 3:
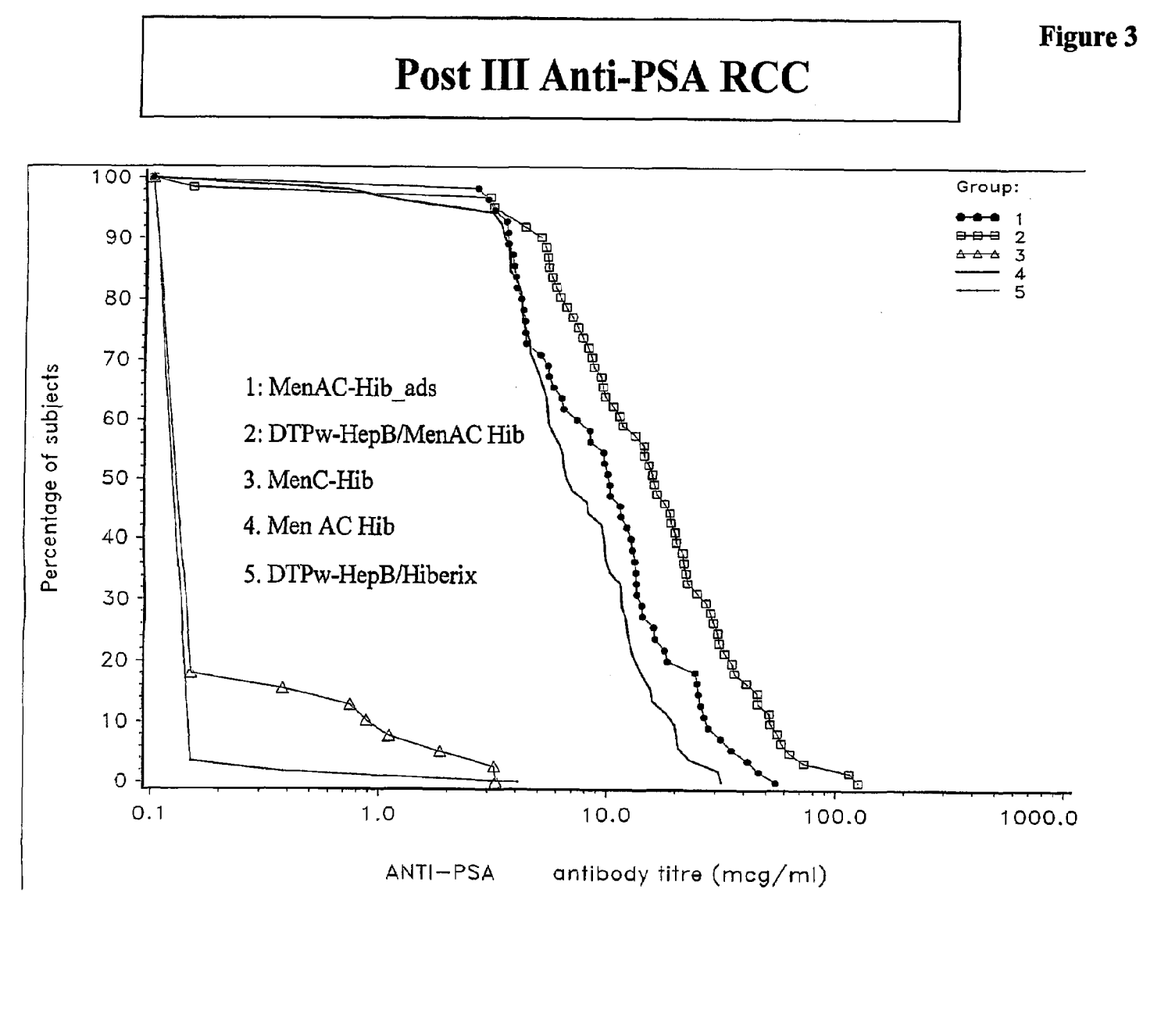
FIG. 3 is a graph (reverse cumulative curve) of the anti-PSA (capsular polysaccharide of meningococcus A) IgG antibody titre (mcg/ml) for each study group of Example 3, showing the percentage of subjects in each study group attaining the antibody titre levels.

This test is an ELISA test that measures IgG content against meningococcal polysaccharide A. FIG. 3 shows the RCC graphs of the data. There is no interference of the MenA polysaccharide antigen to induce at least the same quantity of antibodies when present in a DTPw-HepB/MenAC-Hib vaccine.

Post III Anti SBA Against Meningococcus Serogroup A

| Group | ≥1:8% [L.L.-U.L.] | GMT [L.L.-U.L.] |
|---|---|---|
| MenAC-Hib | 92.5 | 40.1 |
| N = 52 | [79.6-98.4] | [26.2-61.4] |
| MenAC-Hib_ads | 90.9 | 40.6 |
| N = 44 | [78.3-97.5] | [24.5-67.0] |
| MenC-Hib | Not done | Not done |
| N = 0 | | |
| DTPw-HepB/MenAC-Hib | 92.5 | 67.7 |
| N = 50 | [79.6-98.4] | [45.3-101.1] |
| DTPw-HepB/HIBERIX ® | 0.0 | 0.16 |
| N = 57 | [0.0-8.0] | [0.14-0.18] |

This test is a bactericidal test that measures the bactericidal antibodies against meningococcus serogroup A. There is no interference of the MenA polysaccharide antigen to induce at least the same quantity of antibodies when present in a DTPw-HepB/MenAC-Hib vaccine.

Post III Anti PSC (Meningococcus C Capsular Polysaccharide) IgG and SBA-MenC

| Group | Anti-PSC IgG % ≥ 0.3 mcg/ml [L.L.-U.L.] | GMC [L.L.-U.L.] | SBA-MenC % ≥ 1:8 [L.L.-U.L.] | GMT [L.L.-U.L.] |
|---|---|---|---|---|
| MenAC-Hib | 100.0 | 6.9 | 96.1 | 322.5 |
| N = 52/51 | [93.2-100.0] | [5.7-8.2] | [86.5-99.5] | [208.7-498.5] |
| MenAC-Hib_ads | 100.0 | 10.4 | 86.0 | 144.6 |
| N = 55/57 | [93.5-100.0] | [8.6-12.7] | [74.2-93.7] | [87.1-239.8] |
| MenC-Hib | 100.0 | 6.4 | 97.3 | 270.8 |
| N = 40/37 | [91.2-100.0] | [5.2-7.9] | [85.8-99.9] | [167.7-437.3] |
| DTPw-HepB/MenAC-Hib | 100.0 | 12.1 | 91.8 | 394.2 |
| N = 61/61 | [94.1-100.0] | [10.2-14.4] | [81.9-97.3] | [244.8-634.9] |
| DTPw-HepB/HIBERIX ® | 3.5 | 0.16 | 1.7 | 4.4 |
| N = 57/59 | [0.4-12.1] | [0.14-0.18] | [0.0-9.1] | [3.6-5.3] |

Figure 4:
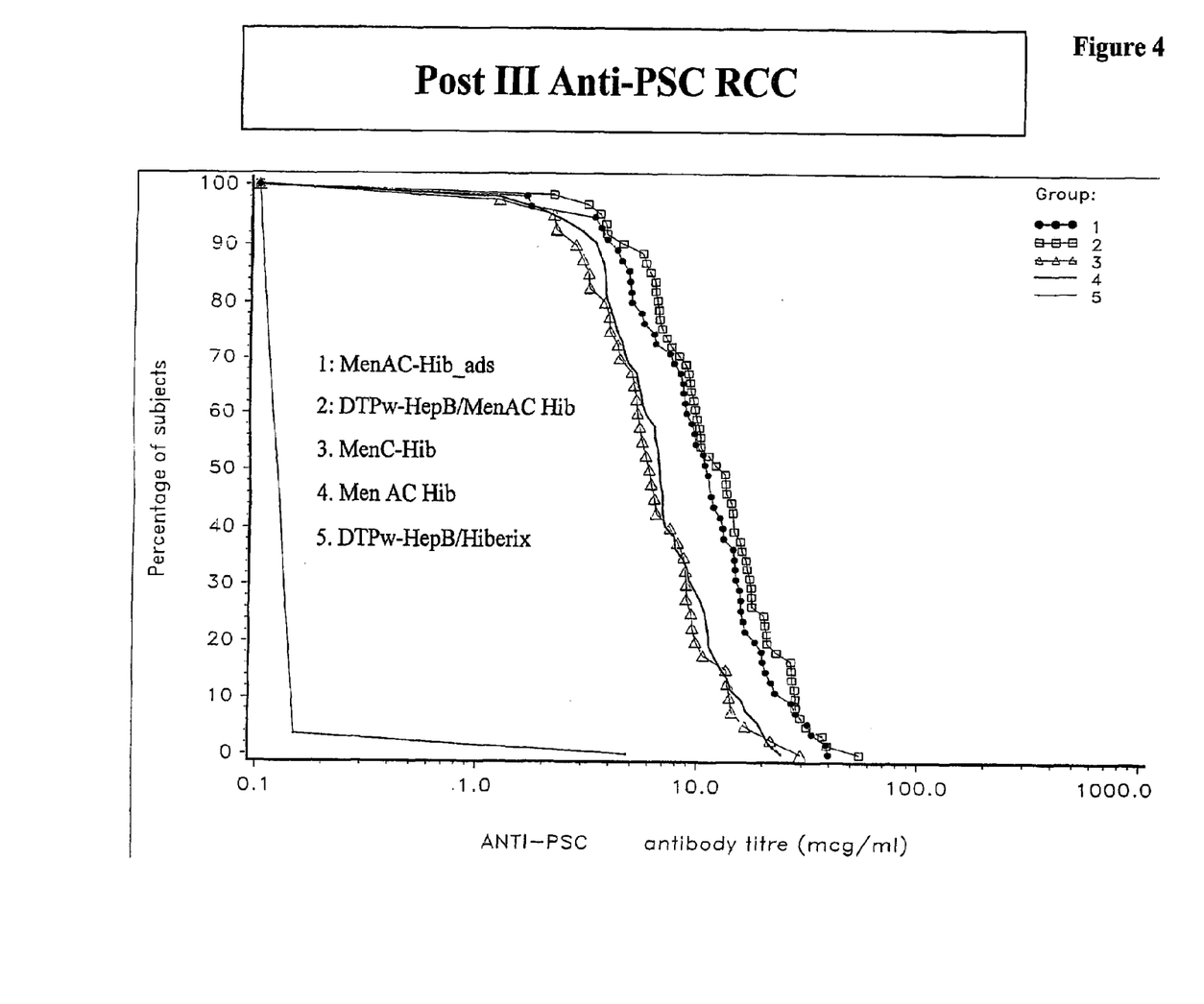
FIG. 4 is a graph (reverse cumulative curve) of the anti-PSC (meningococcal polysaccharide C) IgG antibody titre (mcg/ml) for each study group of Example 3, showing the percentage of subjects in each study group attaining the antibody titre levels.
Figure 5:
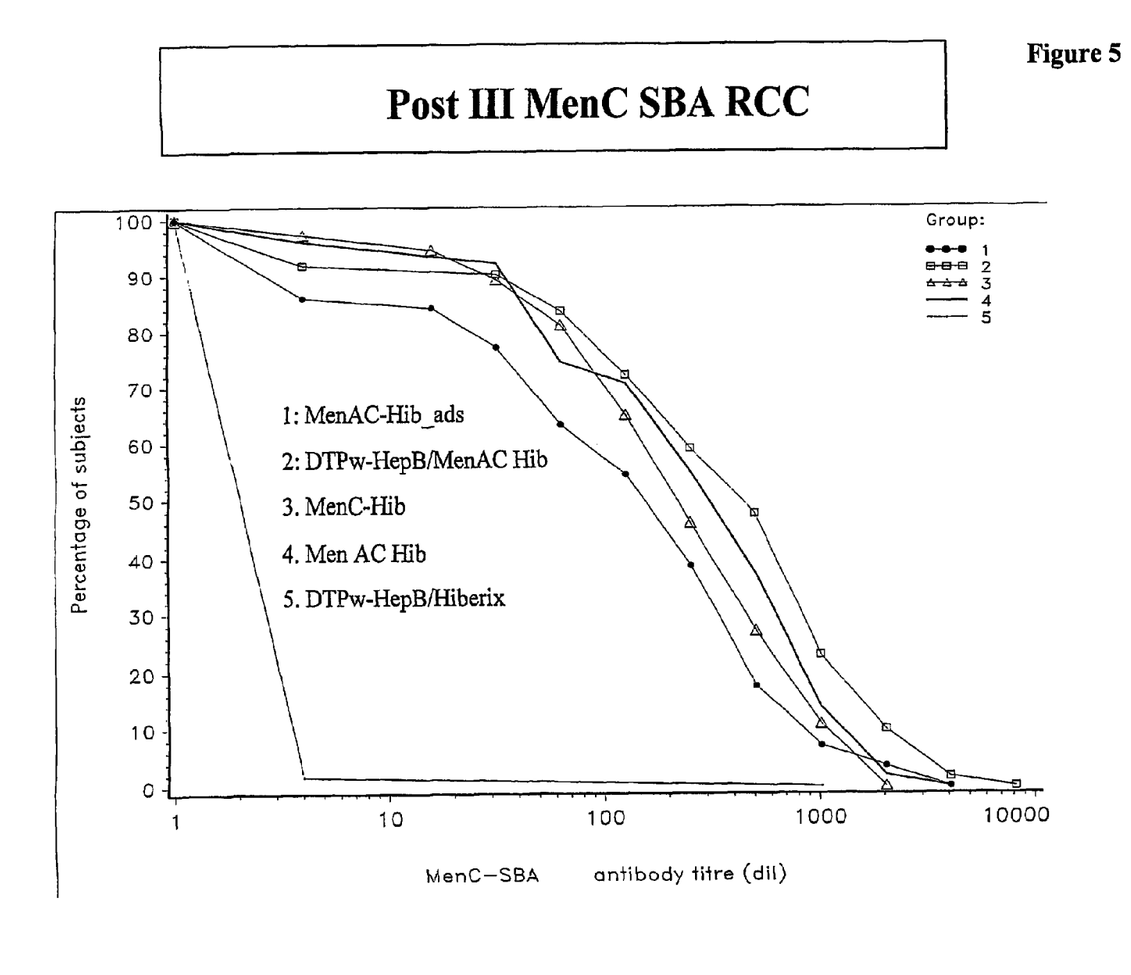
FIG. 5 is a graph (reverse cumulative curve) of the bactericidal activity of serum against meningococcus C for each study group of Example 3, as a measure of functional antibodies.

This test is an ELISA test that measures IgG content against meningococcal polysaccharide C. FIG. 4 shows a RCC graph of the data. SBA-MenC is a bactericidal test that measures the bactericidal activity of the serum against meningococcus C. It is a measure of functional antibodies. FIG. 5 shows a RCC graph of the data. There is no interference on the MenC polysaccharide antigen to induce the same quantity of functional antibodies when it is present in a DTPw-HepB/MenAC-Hib vaccine.

Post III SBA-MenC Against Meningococcus Serogroup C

| Group | SBA-MenC % ≥ 1:8 [L.L.-U.L.] | GMT [L.L.-U.L.] |
|---|---|---|
| MenAC-Hib | 95.1 | 293.4 |
| N = 61 | [86.3-99.0] | [195.6-440.3] |
| MenAC-Hib_ads | 85.1 | 151.4 |
| N = 67 | [74.3-92.6] | [94.2-242.4] |
| MenC-Hib | 96.4 | 297.8 |
| N = 55 | [87.5-99.6] | [201.4-440.4] |
| DTPw-HepB/MenAC-Hib | 93.4 | 426.9 |
| N = 61 | [84.1-98.2] | [271.2-671.9] |
| DTPw-HepB/HIBERIX ® | 1.6 | 4.4 |
| N = 62 | [0.0-8.7] | [3.7-5.2] |

This test is a bactericidal test that measures the bactericidal antibodies against meningococcus serogroup A. It is a measure of functional antibodies. There is no interference on the MenC polysaccharide antigen to induce the same quantity of functional antibodies when it is present in a DTPw-HepB/MenAC-Hib vaccine.

Seroconversion Rates of Antibodies to Diphtheria, Tetanus, B. pertussis Cells and HepB

| Schedule (3-4-5 months) | D | T | BP | HepB |
|---|---|---|---|---|
| MenAC-Hib | 98.5 | 98.5 | 95.5 | 92.5 |
| | [92.0-100] | [92.0-100] | [87.3-99.1] | [83.4-97.5] |
| DTPw-HepB/ MenAC-Hib | 98.5 | 100 | 97.0 | 97.0 |
| | [92.0-100.0] | [94.6-100] | [89.5-99.6] | [89.6-99.6] |
| DTPw-HepB/ HIBERIX ® | 100 | 100 | 97.1 | 97.1 |
| | [94.8-100.0] | [94.7-100] | [89.8-99.6] | [89.9-99.6] |

BP refers to B. pertussis.
An ELISA test was done measuring IgG against the whole cell bacteria.

Geometric Mean Titre (GMT) of Antibodies to Diphtheria, Tetanus, B. pertussis Cells and HepB

| Schedule (3-4-5 months) | D | T | BP | HepB |
|---|---|---|---|---|
| MenAC-Hib | 2.02 [1.62-2.51] | 2.18 [1.69-2.82] | 74.9 [61.9-90.8] | 357.5 [236.2-541.2] |
| DTPw-HepB/MenAC-Hib | 1.69 [1.36-2.09] | 2.42 [1.96-3.00] | 71.6 [59.7-85.9] | 380.2 [265.1-545.2] |
| DTPw-HepB/HIBERIX ® | 1.26 [1.03-1.53] | 2.08 [1.67-2.59] | 69.0 [58.2-81.8] | 379.1 [265.0-542.2] |

From the previous two tables it was observed that the immune response to DT, TT, Pw and HepB are similar to that obtained with the registered TRITANRIX-HEPB™ vaccine in terms of both seroconversion and GMT.

Example 4

Preparation of a Hib—11 Valent Pneumococcal Conjugate (Hib/Strep11V) Vaccine

*H. influenzae* type b capsular polysaccharide conjugated onto TT (10 µg of polysaccharide in the conjugate per dose) which had been lyophilised at a pH of 6.1 in the presence of lactose HIBERIX® (SmithKline Beecham Biologicals)] was extemporaneously (on the same day as use) dissolved in a liquid solution of eleven-valent pneumococcal capsular polysaccharide (serotypes 1, 3, 4, 5, 6B, 7F, 9V, 14, 18C, 19F and 23F) conjugated onto PD (1 µg of polysaccharide in each conjugate per dose). The pneumococcal vaccine had previously been adsorbed onto 0.5 mg $Al^{3+}$ (as $AlPO_4$).

Example 5

Clinical Trials on the Vaccine of Example 4

The vaccine of Example 4 and a control vaccine were administered in a three-dose (3, 4, 5 months of age) schedule to German infants.

The immune response results (measured 1 month after the last primary administration) were as follows.

Anti pneumococcal IgG antibodies: GMC (µg/ml) (ByElisa)

| PS | | Group A | | | Group D | | |
|---|---|---|---|---|---|---|---|
| Antibody | Timing | N | S+ [%] | GMC | N | S+ [%] | GMC |
| Anti-1 | PIII | 30 | 100 | 1.23 | 33 | 100 | 0.99 |
| Anti-3 | PIII | 30 | 100 | 2.04 | 33 | 97.0 | 1.20 |
| Anti-4 | PIII | 30 | 100 | 0.98 | 33 | 100 | 1.03 |
| Anti-5 | PIII | 30 | 100 | 1.33 | 33 | 100 | 1.34 |
| Anti-6B | PIII | 30 | 100 | 0.54 | 33 | 100 | 0.62 |
| Anti-7F | PIII | 30 | 100 | 1.60 | 33 | 100 | 1.33 |
| Anti-9V | PIII | 30 | 100 | 1.61 | 33 | 100 | 1.21 |
| Anti-14 | PIII | 30 | 100 | 2.27 | 33 | 100 | 2.32 |
| Anti-18C | PIII | 30 | 100 | 1.06 | 33 | 100 | 1.04 |
| Anti-19F | PIII | 30 | 100 | 2.05 | 33 | 100 | 1.92 |
| Anti-23F | PIII | 30 | 96.7 | 0.75 | 33 | 100 | 0.76 |

Group A = 11Pn—PD + INFANRIX-HEXA ™ (Infanrix-Penta plus added Hib conjugate)
Group D = 11Pn—PD/Hib + INFANRIXI-PENTA ™
+indicates concomitant (in different limbs) rather than combined administration.

Group A=11Pn-PD+INFANRIX-HEXA™ (Infanrix-Penta plus added Hib conjugate)
Group D=11Pn-PD/Hib+INFANRIXI-PENTA™
Percent of Subjects with Antibody Concentrations No Less than 0.5 µg/ml

| group | PS 1 | 3 | 4 | 5 | 6B | 7F | 7V | 14 | 18C | 19F | 23F |
|---|---|---|---|---|---|---|---|---|---|---|---|
| D | 84.8 | 87.9 | 87.9 | 90.9 | 51.5 | 90.9 | 93.9 | 97.0 | 81.8 | 97.0 | 72.7 |
| A | 86.7 | 96.7 | 76.7 | 90.0 | 50.0 | 93.3 | 90.0 | 90.0 | 80.0 | 96.7 | 66.7 |

Anti PRP Antibodies: GMC (µg/ml) (By Elisa)

| | | Group D (N = 34) | | |
|---|---|---|---|---|
| | | n | ≥1 µg/ml [%] | GMC [µg/ml] |
| Anti-PRP | PIII | 33 | 100 | 10.75 |

100% of subjects had anti-PRP (Hib polysaccharide) antibody concentrations no less than 1.0 µg/ml.

HIBERIX® (unadsorbed Hib-TT conjugate) has a GMC after a similar administration schedule of about 6 µg/ml.

The immune response, in terms of ELISA antibodies, of infants who received the 11Pn-PD/Hib vaccine was similar to that observed for those who received the 11Pn-PD vaccine for all of the serotypes, with the exception of serotypes 1, 3 and 9V for which a trend to lower geometric mean concentrations was observed for the 11Pn-PD/Hib vaccine. However, these differences were not significant as shown by the overlapping of 95% confidence intervals.

The 11Pn-PD/Hib vaccine induced functional (opsonophagocytic) antibodies to all 11 serotypes.

Combining the Hib vaccine with the pneumococcal conjugate vaccine did not significantly interfere with the pneumococcal immune response and surprisingly enhanced the anti PRP response compared to both the registered vaccines INFANRIX-HEXA™ and HIBERIX®.

Example 6

Clinical Trial on the Effect of Lower Amounts of Hib in a DTPwHepB Vaccine

A randomized trial to assess the immunogenicity of a Hib-TT conjugate vaccine at various doses in SB Biologicals DTPwHepB (TRITANRIX™-HB) vaccine was carried out as a primary vaccination in healthy infants at 6, 10 and 14 weeks of age.

544 subjects in four groups (136 each) were administered with the following vaccines: Group 1: DTPw-HepB extemporaneously mixed with a full dose of Hib-TT (PRP 10 µg; TT 10-20 µg; lactose 12.6 µg; aluminium [as salts] 0.15 mg); Group 2: DTPw-HepB extemporaneously mixed with a half dose of Hib-TT (PRP 5 µg; TT 10-µg; lactose 10 µg; aluminium [as salts] 0.0755 mg); Group 3: DTPw-HepB extemporaneously mixed with a quarter dose of Hib-TT (PRP 2.5 µg; TT 5-10 µg; lactose 10 µg; aluminium [as salts] 0.036 mg); Group 4: DTPw-HepB concomitantly administered (in different limbs) with a full dose of Hib-TT.

Geometric Mean Titers (GMTs) of anti-PRP antibodies one month after the third dose were as follows:

| Group | N | GMT | 95% Conf. Interval | |
|---|---|---|---|---|
| 1 | 130 | 14.766 | 11.835 | 18.423 |
| 2 | 124 | 17.304 | 14.209 | 21.074 |
| 3 | 124 | 21.010 | 16.950 | 26.044 |
| 4 | 126 | 22.954 | 18.463 | 28.538 |

The low dose formulation surprisingly has the highest GMT values. This effect should be even greater if the Hib-TT vaccine is unadsorbed.

We claim:

1. A multivalent immunogenic composition comprising the following components:
   (a) killed whole-cell *Bordetella pertussis*,
   (b) tetanus toxoid,
   (c) diphtheria toxoid,
   (d) Hepatitis B surface antigen,
   (e) a conjugate of a carrier protein and the capsular polysaccharide of *Haemophilus influenzae* type B and
   (f) one or more conjugates of a carrier protein and the capsular polysaccharide of a bacterium selected from the group consisting of *Neisseria meningitidis* type A and *N. meningitidis* type C.

2. The multivalent immunogenic composition of claim 1, wherein the composition further comprises one or more conjugates of a carrier protein and the capsular polysaccharide of a bacterium selected from the group consisting of *Neisseria meningitidis* type Y and *N. meningitidis* type W.

3. The multivalent immunogenic composition of claim 1, wherein the capsular polysaccharide of said *Haemophilus influenzae* type B is conjugated to a carrier protein selected from the group consisting of tetanus toxoid, diphtheria toxoid, CRM197, outer membrane protein complex (OMPC) of *N. meningitidis*, and protein D of *H. influenzae*.

4. The multivalent immunogenic composition of claim 1, wherein the capsular polysaccharide of said *N. meningitidis* is conjugated to a carrier protein selected from the group consisting of tetanus toxoid, diphtheria toxoid, CRM197, outer membrane protein complex (OMPC) of *N. meningitidis*, and protein D of *H. influenzae*.

5. The multivalent immunogenic composition of claim 1, wherein the composition further comprises killed, attenuated Hepatitis A virus.

6. The multivalent immunogenic composition of claim 1, wherein the composition further comprises inactivated polio virus.

7. The multivalent immunogenic composition of claim 1, wherein the composition comprises an adjuvant.

8. The multivalent immunogenic composition of claim 7, wherein the adjuvant is aluminium salt.

9. A method of immunizing a mammalian host, the method comprising administering to the host an immunogenic dose of the multivalent immunogenic composition of claim 1.

10. A method of making the multivalent immunogenic composition of claim 1 comprising the step of mixing together the components (a), (b), (c), (d), (e) and (f).

* * * * *